Figure 1:
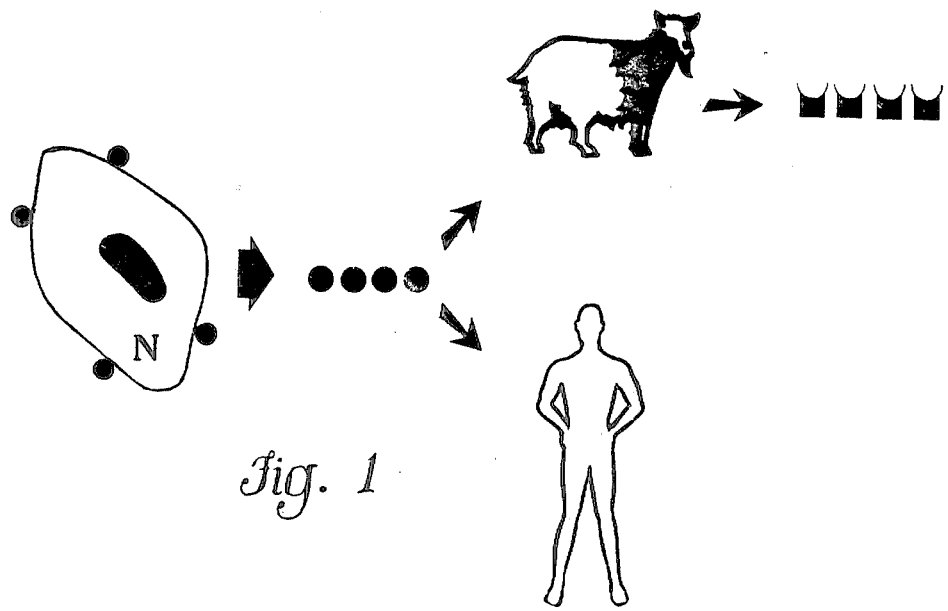

United States Patent [19]

Bartorelli

[11] Patent Number: 4,732,862

[45] Date of Patent: Mar. 22, 1988

[54] DETERMINATION OF CEA BINDING SUBSTANCE USING ANTI-GOAT IMMUNOGLOBULINS

[76] Inventor: Alberto Bartorelli, No. 20, Via Fogazzaro, Milano, Italy

[21] Appl. No.: 671,370

[22] Filed: Nov. 14, 1984

[30] Foreign Application Priority Data

Nov. 21, 1983 [IT] Italy ................ 49370 A/83

[51] Int. Cl.$^4$ ................ G01N 33/053; G01N 33/534; G01N 33/541; G01N 33/537
[52] U.S. Cl. ................ 436/513; 436/536; 436/545; 436/544; 436/538; 436/540; 436/811; 436/813; 436/825
[58] Field of Search ................ 436/536, 513, 538, 539, 436/540, 545, 813, 544, 811, 825

[56] References Cited

U.S. PATENT DOCUMENTS 4,178,359 12/1979 Mondabaugh et al. ........ 436/538 X
4,299,815 11/1981 Hansen et al. ................ 436/540

OTHER PUBLICATIONS

K. Kapsopoulou–Dominos & F. A. Anderer, "An Approach to the Routine Estimation of Circulating Carcinoembryonic antigen Immune Complexes in Patients with Carcinomata of the Gastrointestinal Tract"–Clin. Exp. Immunol (1979) 37, 25–32.
J. M. MacSween, "The Antigenicity of Carcinoembryonic Antigen", Int. J. Cancer 15, 246–252 (1975).
Phil Gold and S. O. Friedman, "Demonstration of Tumor–Specific Antigens in Human Colonic Carcinomata by Immunological Tolerance and Absorption Techniques", J. Exp. Med. 121, 439 (1965).
P. LoGerfo et al, "Absence of Circulating Antibodies to Carcinoembryonic Antigen in Patients with Gastrointestinal Malignancies", Int. J. Cancer: 9, 344–348 (1972).
E. Collatz et al, "Further Investigations of Circulating Antibodies in Colon Cancer Patients: On the Autoantigenicity of the Carcinoembryonic Antigen", Int. J. Cancer 8, 298–303 (1971).
K. Kapsopoulou–Dominos et al, "Circulating Carcinoembryonic Antigen Immune Complexes in Sera of Patients with Carcinomata of the Gastrointestinal Tract", Clin. Exp. Immunol (1979), 35, 190–95.
J. M. Gold et al, "Human Anti–CEA Antibodies Detected by Radioimmunoelectrophoresis", Nature New Biology 238, 60–62 (1972).
G. M. Mavligit et al, "Colorectal Carcinoma", 0008–543X/0701/0146, American Cancer Society.

Primary Examiner—Sidney Marantz
Assistant Examiner—Jack Spiegel
Attorney, Agent, or Firm—Beveridge, DeGrandi & Weilacher

[57] ABSTRACT

A method is disclosed for the determination of human serum factors which are specific for human carcinomata antigens, in which method the serum of a patient with a carcinoma is incubated with CEA that has been radioactively labeled and anti-goat immunoglobulin serum in toto or depleted of the cross-reaction capacity for human IgA, IgG and IgM is added, then the whole mass is incubated and centrifugated, the supernatant is decanted and the precipitate is counted with a gamma counter. These specific serum factors are employed as a marker of primitive tumoral forms.

5 Claims, 3 Drawing Figures

DETERMINATION OF CEA BINDING SUBSTANCE USING ANTI-GOAT IMMUNOGLOBULINS

The present invention relates to a method for the determination of human serum factors specific for human carcinomata antigens as well as to the employment of said method in the serodiagnosis of primitive tumoral forms. More particularly, this invention is concerned with a procedure for isolating free specific substances in human sera from patients with carcinomata, said substances being capable of binding radioactively labeled CEA in vitro in a specific way and of reacting in immunohistochemical tests with carcinoma cells only.

As it is well known, no procedures or experimentations exist up to date capable of showing the presence of free tumor-specific immunoglobulins in the sera of patients with carcinomata (see for example DOMINOS K. KAPSOPOULOU, and F. A. ANDERER, "An approach to the routine estimation of circulating carcinoembryonic antigen immunocomplexes in patients with carcinomata of the gastrointestinal tract" Clin. Exp. Immunol. (1979) 37, 25–32).

Indeed, it was already well known that the carcinoembryonal antigen (CEA) described the first time by P. Gold and S. O. Freedman ("Demonstration of tumor specific antigen in human carcinomata by tolerance and absorption technique", J. Exp. Med. 121, 439, 1965), was employed as a functional marker for controlling the post-operative follow-up of patients with gastrointestinal carcinomata whereas its determination had been shown of little use in the early diagnosis and in general in the diagnosis of primitive carcinomata in the absence of metastases. Successively, the problem of the induction of an immunoreaction or anyway the formation of CEA-binding specific substances on the part of CEA in patients with CEA-secreting carcinomata, formed a subject of long experimentation though with results which were not sufficient to give a satisfying answer to that problem. More particularly, various attempts are known (Lo Gerfo P., Herter F. P. and Bennett S. J. (1972) "Absence of circulating antibodies to carcinoembryonic antigen in patients with gastrointestinal malignancies" Int. J. Cancer 9, 344, E. Collatz, Von Kleists, and P. Burtin (1971) "Further investigations of circulating antibodies in colon cancer patients: on the autoantigenicity of the carcinoembryonic antigen" Int. J. Cancer 8, 298) to show the presence in the serum from patients with carcinomata of specific antiCEA antibodies, but such attempts were completely unsuccessful.

Just in 1972 (J. M. Gold, S. O. Freedman and P. Gold (1972) "Human AntiCEA antibodies detected by radioimmunoassay" Nature, New Biology 238, 60–62) immunoglobulins of the IgM class were shown by radioimmunoelectrophoresis to be present in the sera of some patients and capable of linking the CEA. However, such a result was confuted by many other Authors (see in particular K. Dominos Kapsopoulou, F. A. Anderer, "Circulating carcinoembryonic antigen immunocomplexes in sera of patients with carcinomata of the gastrointestinal tract", Clin. Exp. Immunol. (1979) 35, 190–195).

The existence was also proved (J. M. MacSween "The antigenicity of circulating antibodies to carcinoembryonic antigen with gastrointestinal malignancies" Int. J. Cancer 1975, 15, 246–252) of a weak and non specific bond (because due to a cross-reaction with the blood groups) between the IgMs present in the sera of some patients and the radioactively labeled CEA ($^{125}$I-CEA). Some references are also known (Gloria M. Mavligit and Sarah Stuckey "Colorectal carcinoma, Evidence for circulating CEA-anti-CEA complexes" Cancer 52, 146–149, 1983) that point out the presence of CEA-anti-CEA circulating immunocomplexes in which the immunoglobulins are considered both as of the IgM and of the IgG types.

Hence it is very clear that the acquisition of a method according to the present invention is of an exceptional importance, because said method allows on one side the determination of the presence of a CEA-binding substance (CBS) which was unknown up to date in the human sera of CEA-secreting carcinomata bearers and, on the other side, the supplying of basic means for an early serodiagnosis of tumoral affections.

In addition to that implication, whose contribution to a future dynamics of a therapeutic and antitumoral prevention program is by all means of an extraordinary and unforeseeable purport, it is also evident how other advantageous uses of said CBS as a marker can be derived from the result supplied by the finding of the present invention, said marker being free from the risks of anaphylactic shocks, both for drugs and for the definite localisation of the tumoral site.

Figure 3:
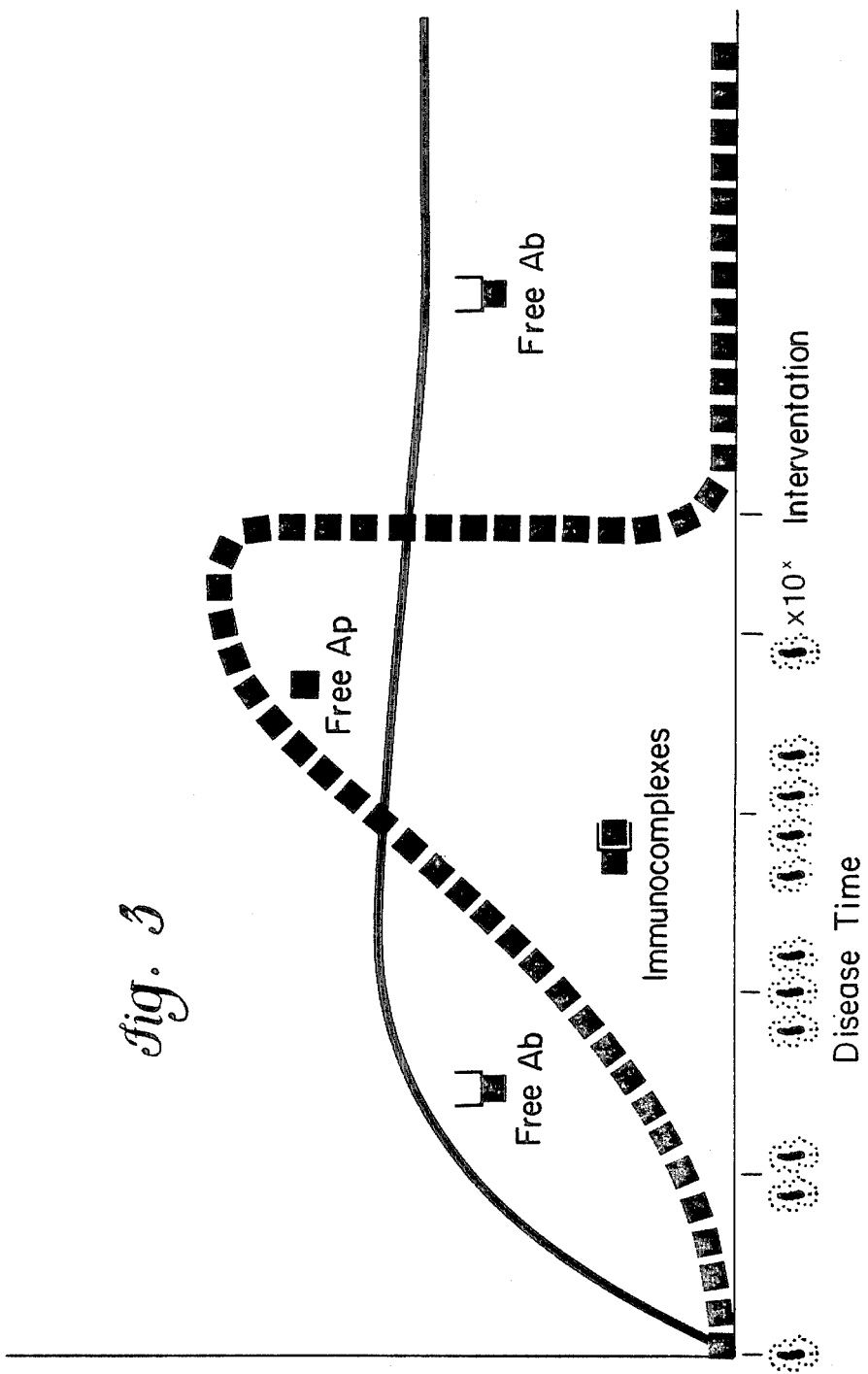

For the acquisition of said results, a method is suggested according to the present invention which is based operatively on the preliminary remark that if a tumoral cell binding specific substance is an actually existing entity, it is likely present in the free state in the sera of carcinomata-bearer patients in the initial phase of the disease, in which, as is well known, such sera show negative in the usual methods of determination of CEA. In this period there is a high antibody reaction in presence of a little amount of antigen and therefore free circulating substances like CBS can be found (FIG. 3). On the basis of the already known knowledge (British patent application 8317022 in the name of the same applicant) of the presence of new antigenic determinants in the adenocarcinomata, it was observed according to the invention that said CBS cannot be detected by the usual immunochemical procedures (immunoelectrophoresis, Agar double diffusion, double antibody radioimmunoassay) employing human anti IgM anti IgG and anti IgA sera (Behring-Werke).

In such a context, according to the present invention the precipitation is suggested of CBS by employing antigoat sera (as for instance anti-goat immunoglobulins sera produced in rabbit, etc.) and anti-guinea pigs sera which, however are less active as to the amount of the precipitate. Indeed, as is well known, antigoat sera are capable of reacting with human immunoglobulins (interspecies cross-reaction), so that if antigoat sera are depleted of such a cross-reaction capability as regards human IgA, IgM and IgG by bioabsorption, they go on with precipitating CBS which therefore appears to be a human serum component not pertaining to the already known classes of immunoglobulins and is present only in carcinomata-bearers sera only. More particularly, as a confirmation of the specific character of CBS, it was observed that if the serum of a patient which is shown to be positive for said substance is incubated with the serum of a patient which is shown to be positive for the circulating CEA, (that is when the amount of circulating CEA is high), the serum of the first patient (CBS positive serum) loses any capability of bonding the radioactively labeled CEA, and the same also occurs if the serum of the first patient is incubated with CEA extracted from carcinomata.

Accordingly, the activity of CBS is demonstrable in the sera of patients in the initial stage of the tumoral disease, as is shown by checks carried out on breast carcinomata kept under control, and, after surgical intervention, in the full absence of the tumoral cells (FIG. 3). So it is clear that CBS can be of an extraordinary use as a marker of a very early tumor, independently of the tumoral mass. Indeed, as is well known, a very low antigen concentration is sufficient to give a very good antibody response, whereas, as discussed above, the antigen can be employed as a marker just when its blood concentration is very high ($>9.5 \times 10^{-9}$ g/ml), i.e., when the size of the tumoral mass is very high. Evidently, according to the present invention anti-human-CBS may be used as an alternative to anti-goat serum from rabbit.

In any case, when the precipitation has been carried out and CBS bonded to the excess radioactively labeled CEA added has been centrifugally separated, a simple gamma counting confirms the isolation as well as the amount of the new antibody which is present in the sera of the patients.

Thus, it is a specific object of the present invention a procedure for the determination of specific substances which are specific for human carinomata antigens (CBS Factor), said procedure being characterized in that it comprises the following operations:

the incubation of the serum of a patient which is a carcinomabearer with radioactively labeled CEA ($^{125}$I-CEA) (50.000 cpm, 80 $\mu$Ci/$\mu$g of specific activity) for at least 16 hours at room temperature (the first incubation);

the addition of anti-goat immunoglobulin antiserum in toto or depleted of its cross-reaction for the human IgA, IgG and IgM, and the incubation for 1 hour at room temperature (the second incubation);

centrifuging and decanting the supernatant and counting the precipitation with a gamma counter.

By preference according to the present invention an anti-CBS rabbit antiserum is employed. As was already discussed, anti-CBS antisera obtained from different animal species can also be employed as an alternative.

For instance, CBS is extracted from the sera of numerous patients which were shown to be positive to the radioimmunological test (caprylic acid, PEG, etc.), said CBS being also purified further from the other human immunoglobulins by various procedures such as ionic exchange, molecular sieve techniques or by affinity and bioabsorption, and the CBS so purified is employed for the immunization of rabbits according to the procedure disclosed above (antigoat).

The present invention will be disclosed in the following for illustrative and not for limitative purposes by means of examples of a preferred procedure.

REAGENTS AND THEIR PREPARATION (a) Rabbit-anti-goat immunoglobulins (anti-goat serum)

Goat immunoglobulins are extracted from the common goat serum by the usual procedures (polyethylene glycol (P.E.G.) caprylic acid, etc.). 1 ml (2 mg/ml) of that extract is injected with the Freunds adjuvant (1 ml) into a rabbit once every fortnight for two months. Immunoglobulins are extracted (P.E.G.) from the rabbit serum, the anti-goat titer is checked by the RIA (the radioimmunoassay) according to the usual double antibody procedures that have been employed as laboratory techniques for ten years.

(b) The anti-goat cross-reaction with the normal human immunoglobulins; check and depletion (elimination of the cross-reaction)

With the techniques of immunoelectrophoresis and of Agar double diffusion, the anti goat serum exhibits its cross reaction with human IgA and IgG (it cannot be recognized with the IgM reaction). The anti goat serum is made to percolate many times through a bioabsorption column (the affinity chromotography procedure) with Sepharose bonded to the IgA, IgG immunoglobulins and, for the sake of certainty, also to the human IgM immunoglobulins. After such purification procedure, the absence of said cross reaction is checked by the techniques reported above. The cross reaction is thus depleted on the average by 30%. The anti-goat serum so depleted keeps obviously capable to respond with the goat immunoglobulins.

(c) Anti-human-immunoglobulins rabbit serum. Anti IgM anti IgA anti IgG serum

For the sake of accuracy, the Behring Werke sera have been employed because they can be considered as a universally recognized means for checking purposes.

(d) Pure CEA-radioactively labeled CEA (e) Determination of CBS specific Factor in the sera of patients with carcinomata (the radioimmunological test)

Human serum amounts scaled in the range from 0.1 to 0.5 ml are incubated for 16 hours at room temperature with 0.1 ml of $^{125}$I-CEA (corresponding to 50.000 cpm) in a PBS 0.05 m buffer +0.1% bovine albumin at pH 7.4. At the end of the first incubation (between the eventual CBS and the tumoral radioactively labeled antigen) 0.1 ml of 1/10 anti-goat serum from rabbit or anti-CBS from rabbit is added (that causes the precipitation of the immunocomplexes formed between said CBS and the $^{125}$I-CEA), then the mass is centrifuged for 15 minutes at 4,000$\times$g. The supernatant is decanted. The precipitate so isolated is counted by a gamma counter.

The precipitate formed with CBS negative sera was never higher than 1,000 cpm, whereas positive sera gave radioactivity values from 1500 up to 32,000 cpm.

(f) Immunologic differences between CBS Factor and the IgA, IgM or IgG

If the anti-goat serum is substituted with an anti-goat serum depleted according to the procedure disclosed above, the results obtained with positive sera are the same.

If the anti-goat serum is substituted with human anti-IgA, anti-IgM or anti-IgG, i.e., with antisera obtained (in the rabbit, the ass, etc.) against the human IgA, IgM and IgG immunoglobulins, no precipitation is obtained.

(g) CBS Factor specifity-Demonstration

When CBS positive serum is incubated with the sera of healthy donors, the CBS activity persists.

If the serum of a healthy donor is substituted with the serum of a CEA-positive patient, CBS activity is no longer detectable; more exactly, the free CEA "blocks" the active sites of CBS so that the $^{125}$I-CEA cannot be bonded any more.

CBS shows immunohistochemical responses with carcinomata cells only and not with other cells.

Figure 2:
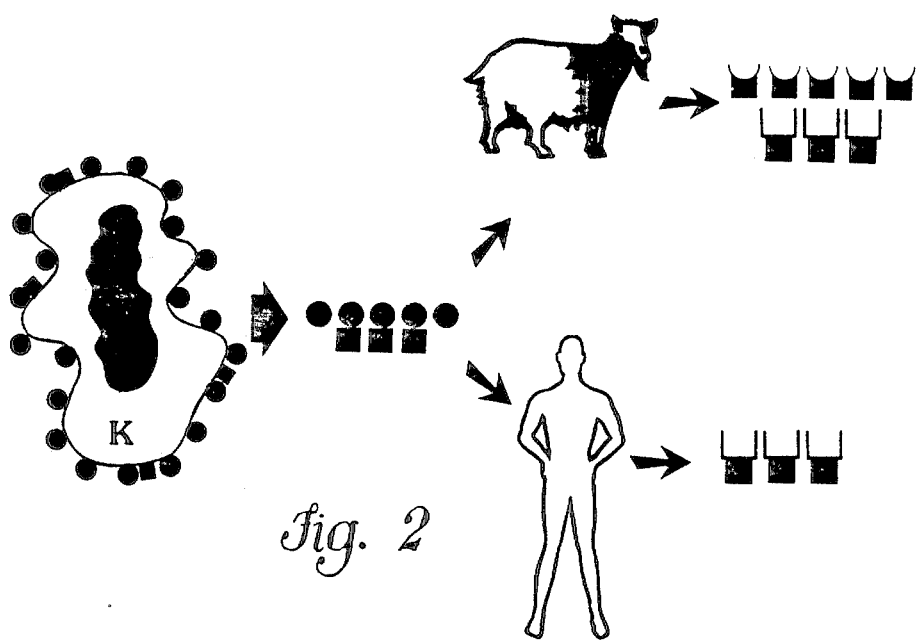

For a better understanding of the procedure of the present invention, reference is made to FIGS. 1, 2 and 3 of the enclosed drawings, in which the formation of antibodies is reported on injection of human serum from a healthy bearer (FIG. 1) and from a patient with carcinoma (FIG. 2) into the goat and the man. More exactly, these Figures contribute to explain the inventive concept. The little balls represent the membrane antigens which are common to the normal cells (N) and to the tumor cells (K). It is clear that the human antigens (N) induce an immunoreaction when injected in a goat (Xenogenic), but not in the man. So, the injection of a tumoral extract in a goat determines a mixed immunoreaction: non-specific antisera (directed against antigens (N)) and specific antisera (directed against tumor-specific antigens (K)). Said specific antisera or anyway said substances which are active in bonding the $^{125}$I-CEA at RIA or the tumoral cells in immunohistochemical tests have been called CBS (CEA Binding Substances) in this specification.

A diagram is shown in FIG. 3 illustrating the concentration (Ab) of the free and bonded CBS and (Ag) of the specific free antigens as the ordinate as a function of the time of disease as the abscissa.

As a concluding remark, it is to be observed that in the sera of patients with carcinomata, both CEA and the specific CBS are present. Such CBS factors show no response to the human anti-(IgA, IgM and IgG) sera, whereas they show cross-reaction responses to anti-goat sera which, as is well known, do not react with common human immunoglobulins if they are depleted.

It is to be observed that results obtained up to the present time in the experimentations carried out with 30 patients (240 healthy checks) with (primitive, post-operative, or with metastasis) carcinomata, allow to hypothesize in a quite reasonable way the occurrence of an immunological mechanism of the following kind (FIG. 3):

Stage I—a tumor preliminary stage or the immunization stage.

Few tumoral cells put into circulation low concentrations of the antigen (CEA) which immunize the organism, which last responds producing a high concentration of CBS; in this stage, CBS is found in the serum, but not free antigen is observed, because it is completely bonded to the immunoglobulins (see FIG. 3).

Stage II—The tumoral mass increases in its sizes, and the antigen concentration increases also, whereas the concentration of CBS increases at a very lower degree (immuno-depression); hence an always decreasing concentration of free CBS is observed in the circulation; all CBS is bonded to the antigen: the stage of the immunocomplexs.

Stage III—The tumoral mass increases in size so as to produce an antigen concentration higher than the CBS concentration; the amount of the free antigen can be determined; the stage of the CEA positive determinations whereas immunoglobulin cannot be determined.

Stage IV—The intervention. The antigen concentration decreases to very low values whereas the CBS titer keeps constant; because, as is well known (for instance tuberculon's) in the absence of antigen.

Stage V—Metastases: the antigen starts to be present again, with induction to form new specific antibodies.

The present invention has been disclosed with particular reference to some specific embodiments but it is to be understood that modifications and changes can be introduced in the above disclosure without departing from its true spirit and scope, for which a priority right is claimed.

I claim:

1. A method for the determination of CEA binding substance (CBS), which comprises incubating the serum of a patient with carcinoma in a first incubation with CEA that has been radioactively labeled ($^{125}$I-CEA, 50,000 cpm, 80 $\mu$Ci/$\mu$g of specific activity) for at least 16 hours at room temperature;

adding anti-goat immunoglobulin antiserum in toto or depleted of the cross-reaction capacity for human IgA, IgG and IgM; and incubating in a second incubation for 1 hour at room temperature; and centrifuging and decanting the resulting supernatant; and counting the resulting precipitate with a gamma counter.

2. A method according to claim 1, wherein said antiserum is an anti-goat antiserum produced in a rabbit.

3. A method according to claim 2, wherein amounts of human serum scaled within the range from 0.1 to 0.5 ml are incubated in said first incubation at room temperature with 0.1 ml of $^{125}$I-CEA (50,000 cpm in 0.05 m PBS buffer+0.1% bovine albumin, at pH 7.4) and in said second incubation, 0.1 ml of said anti-goat serum are added, this addition being followed by 15 minutes centrifugation at 4,000×g, and by decantation of the supernatant and by counting of the precipitate with a gamma counter.

4. A method according to claim 2, wherein said anti-goat serum is depleted of cross-reaction capacity for the IgA, IgG and IgM immunoglobulins through a bioabsorption process carried out by percolation through Sepharose bonded to the IgA, IgG and IgM immunoglobulins.

5. A method according to claim 1, wherein the addition preceding the second incubation is performed with anti-goat immunoglobulins produced in rabbit, ass or horse.

* * * * *